United States Patent
Schwebel

(10) Patent No.: US 6,886,933 B2
(45) Date of Patent: May 3, 2005

(54) REMEDY FOR DRY EYE SYNDROME

(76) Inventor: Mary L. Schwebel, 4 Park La., Minneapolis, MN (US) 55416

(*) Notice: Subject to any disclaimer, the term of this patent is extended or adjusted under 35 U.S.C. 154(b) by 0 days.

(21) Appl. No.: 10/645,718

(22) Filed: Aug. 21, 2003

(65) Prior Publication Data

US 2004/0051841 A1 Mar. 18, 2004

Related U.S. Application Data

(63) Continuation of application No. 10/123,604, filed on Apr. 15, 2002, now Pat. No. 6,641,264.

(51) Int. Cl.⁷ ............................................. G02C 11/08
(52) U.S. Cl. ...................... 351/62; 351/155; 351/158; 604/294; 604/300
(58) Field of Search ........................... 351/41, 62, 155, 351/158; 604/294, 300; 2/12

(56) References Cited

U.S. PATENT DOCUMENTS

| | | |
|---|---|---|
| 5,307,095 A | 4/1994 | Ogura |
| 5,627,611 A | 5/1997 | Scheiner |
| 6,270,467 B1 | 8/2001 | Yee |
| 6,312,125 B1 | 11/2001 | Potts |
| 6,312,403 B1 | 11/2001 | Ruiz |
| 6,641,264 B1 * | 11/2003 | Schwebel .................... 351/62 |

FOREIGN PATENT DOCUMENTS

JP 2002-5216 1/2000

OTHER PUBLICATIONS

BD e–Catalog, Ophthalmology Products, 2001, pp 1–2.
BD e–Catalog, Ophthalmology Products, Product No. 581040, 2001, pp1–3.
EV EagleVision, Solutions for Better Vision, Our Products, 2002, pp 1–5.

* cited by examiner

Primary Examiner—Huy Mai
(74) Attorney, Agent, or Firm—Patterson, Thuent, Skaar & Christensen, P.A.

(57) ABSTRACT

A treatment for dry eye syndrome. An at least partially sealed chamber including a reservoir for moisture for surrounding the eyes is disclosed. The invention may be transparent for use during the day or in association with prescription or non-prescription lenses. The moisture chamber may also be opaque to act as a blackout mask for sleeping.

37 Claims, 2 Drawing Sheets

REMEDY FOR DRY EYE SYNDROME

RELATED APPLICATION

This application is a continuation of application Ser. No. 10/123,604 filed Apr. 15, 2002 now U.S. Pat. No. 6,641,264.

FIELD OF THE INVENTION

The present invention relates to the treatment of dry eye syndrome. More particularly, it relates to altering the local environment to reduce the discomfort of dry eye syndrome.

BACKGROUND OF THE INVENTION

Dry eye syndrome is one of the most commonly treated eye problems in the United States. Dry eye syndrome is also known as keratitis sicca, keratoconjunctivitis sicca (KCS) xerophthalmia, and lacrimal insufficiency. It is estimated that over ten million Americans and 30 million persons worldwide suffer from dry eye syndrome.

For a large fraction of dry eye patients, dry eye syndrome creates discomfort or annoyance. For those severely afflicted, dry eye syndrome can be debilitating and, in some circumstances, even sight-threatening. In extremely severe cases, dry eye syndrome can even lead to the loss of an eye.

Dry eye syndrome typically results from deficiency in the quality or quantity of tears produced by the patient. Precorneal tear film has traditionally been considered to have a three-layered structure. The closest to the cornea lies the mucin, or mucus, layer. The mucin layer provides an interface between the corneal epithelium and the remainder of the tear film. Overlying the mucin layer is the watery aqueous layer, which is the thickest layer of the three. The outermost layer of the precorneal tear film is the lipid layer. The lipid layer is an oily film that reduces evaporation from the aqueous layer beneath it.

The middle aqueous layer provides moisture to the corneal tissue, carries important nutrients, and serves to remove metabolic waste produced by the cornea. Deficiency in any of the three layers of the precorneal tear film can result in complaints of dry, gritty feeling or burning eyes.

The mucin that forms the mucin layer, nearest the cornea, is secreted by goblet cells in the conjunctiva. The conjunctiva is the transparent tissue that covers the sclera and the backside of the eyelids. The mucin layer functions to decrease surface tension of the tear film. In addition, the cornea itself is hydrophobic. Without the mucin layer to provide a bridge between the cornea and the aqueous layer, the aqueous layer would bead up and allow dry spot formation on the cornea.

The aqueous layer is secreted primarily by the glands of Wolfring and Krause located in the eyelid margin. The aqueous layer helps provide an optically smooth, transparent surface to the precorneal tear film. The lipid layer is secreted by the meibomian glands, and the glands of Zeiss and Moll. The glands of Zeiss and Moll are also located at the eyelid margin.

Blinking is essential to maintenance of the precorneal tear film. During each blink, the eyelid wipes over the surface of the cornea, smoothing the mucin layer and spreading the overlying aqueous and lipid layers to provide a completely wetted surface. In between blinks, the tear film thins due to evaporation of the aqueous layer. If evaporation is excessive, dry spots may form on the surface of the cornea.

Deficiency, or imperfect quality, of any of the three component layers can lead to dry eye symptoms. Many systemic and external factors can contribute to dry eye syndrome. For example, Sjogren's syndrome is associated with arthritic diseases in combination with dry eye and dry mouth. Deficiency of Vitamin A, use of oral contraceptives and environmental factors can all contribute to dry eye syndrome.

Recent research into the natural history of dry eye syndrome has shown that the disease progresses through four stages. Each stage is a consequence of the preceding stage. The stages are:

1. Loss of water from the aqueous layer of the tear film leading to an increase in the tear film osmolarity;
2. Loss of conjunctival goblet cells and decreased corneal glycogen;
3. Increased loss of corneal squamous epithelial cells;
4. Destabilization of the interface between the corneal surface and the tear film.

Either decreased secretion of tear film components or increased evaporation lead to increased tear film osmolarity and the following stages that lead to eventual corneal decompensation and the serious consequences of dry eye syndrome.

The adnexa of the eye may also be involved in dry eye syndrome. The adnexa of the eye include the structures surrounding the eye such as the eyelids, eye lashes, the tear drainage and tear production structures. Blepharitis commonly contributes to dry eye syndrome. Blepharitis typically results from bacterial infection of the tiny glands in the margin of the eyelid. These glands include the glands of Zeiss, Moll and Wolfring as well as the meibomian glands. Most commonly, the affected glands are the meibomian glands. In bacterial blepharitis, bacterial infection causes the meibomian glands to become plugged, and thus not be able to produce a normal lipid layer to contribute to the tear film. Some bacteria that infect the glands also secrete exotoxins that seep out of the glands into the eye and injure the corneal epithelium.

Treatments of dry eye syndrome vary depending upon the type of presentation. The most common treatment for dry eye syndrome is the use of artificial tear supplements to provide additional moisture and lubrication to the corneal surface. Artificial tear eye drops are placed on the eye by the patient. Artificial tear supplements must be used regularly and often to be effective.

Lubricant ointments may also be employed. Ointments are usually used at bedtime because they tend to be messy and blur vision. For some patients, even the use of ointments is not sufficient to provide comfort during sleep.

Tears drain from the eye through the lacrimal drainage system. Tiny openings at the nasal corner of each upper and lower eyelid are called the lacrimal puncta. The lacrimal puncta lead into ducts that drain into the nasopharynx.

One treatment for dry eye syndrome is to partially or completely close one or more lacrimal puncta to reduce tear outflow into the lacrimal drainage apparatus. Traditionally, this closure was accomplished surgically or by cautery. In the last decade, however, temporary and permanent punctal occlusion plugs have been utilized.

Permanent punctal plugs are typically made from surgical silicone; temporary plugs are generally made of soluble collagen. Collagen plugs dissolve over a period of days and are helpful in diagnosis.

Punctal plugs are placed into the lacrimal puncta, or lacrimal drainage ducts. The plugs impede the outflow of tears from the eye. This approach slows the outflow of tears and retains them in the eyes longer, often relieving symptoms. Punctal plugs have the distinct advantage of being readily removable and avoid the issues of scar formation.

Blepharitis is sometimes treated by the use of antibiotic medications. Another important treatment for blepharitis is the application of warm soaks and lid scrubs. In this form of treatment, the patient applies a warm wet washcloth to the eyelids for a period of time to provide humidity, warmth and to help soften blockage of and restore flow from the meibomian glands. Lid scrubs are practiced by taking a mild, nonirritating soap and vigorously scrubbing the eyelid margins with they eyes closed, so as to massage the meibomian glands and increase production. The surfactant helps to dissolve the greasy blockage of the meibomian glands.

Patients who have severe dry eye syndrome often suffer disrupted sleep because they cannot go for longer than an hour or so without applying tear supplements to the eyes. This can lead to pronounced sleep deprivation and a consequent reduction in quality of life.

A variety of researchers have been seeking other medicinal treatments for dry eye syndrome. Largely, this research is directed at pharmaceutical efforts to increase tear production.

Despite the many treatment options available, there remains no cure for dry eye syndrome. A great many patients still have substantial and even debilitating discomfort because of dry eye syndrome. Very few treatment options exist to provide comfort for dry eye syndrome patients during sleep.

SUMMARY OF THE INVENTION

The invention generally includes an at least partially enclosed chamber at least partially sealed around the eyes and a reservoir for water or another liquid subject to evaporation to provide a high humidity environment in the vicinity of the eyes. The invention may incorporate a blackout mask for use while sleeping or may incorporate a transparent front structure to accommodate nonprescription or prescription lenses. Another embodiment of the invention may be incorporated into a hat with a brim.

The invention benefits the patient by increasing comfort and ameliorating the damaging effect of dry eye syndrome on the patient's eyes. The invention also improves the ability to of the patient to achieve a normal sleep cycle of 6 to 10 hours.

DETAILED DESCRIPTION OF THE INVENTION

Figure 1:
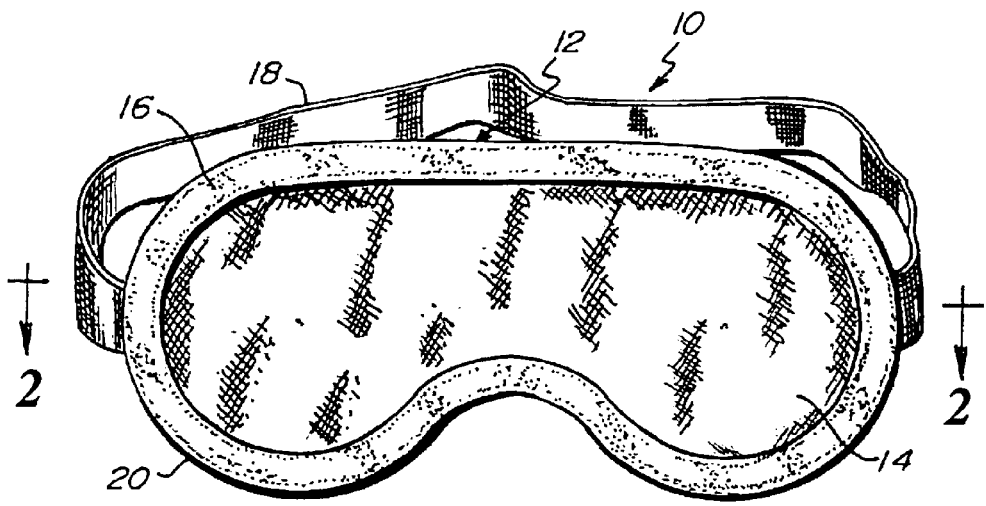
FIG. 1 is a rear plan view of a first embodiment of a pre-corneal humidity chamber in accordance with the present invention.

Referring to FIG. 1, a first embodiment of a pre-corneal humidity chamber 10 is depicted. This embodiment generally includes a sleep mask 12, moisture reservoir 14, seal 16 and retaining member 18.

Sleep mask 12 is preferably made of a moisture impermeable and flexible material. Sleep mask 12 is shaped and sized appropriately to conform to the area surrounding the eyes and orbit in a comfortable fashion. Sleep mask 12 is preferably shaped so that the perimeter 20 thereof fits snuggly against the skin of the face.

Moisture reservoir 14 may include any type of device adapted to contain and release a material subject to evaporation or sublimation. Examples include an absorbent fibrous substance, a chamber for holding a material subject to vaporization and a chemical mixture that releases as a vapor desired substance.

Figure 2:
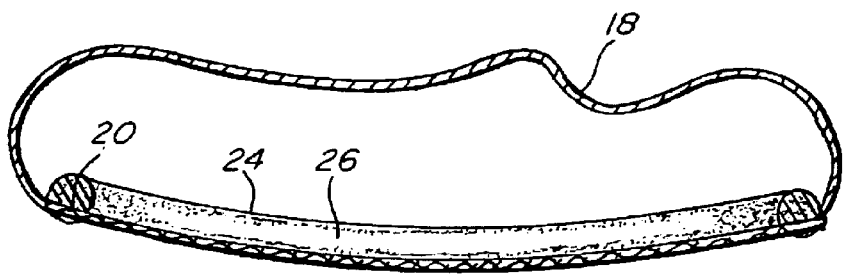
FIG. 2 is a sectional view of the pre-corneal humidity chamber of FIG. 1.

Seal 16 generally conforms to perimeter 20 of sleep mask 12. Sleep mask 12 may also be configured without seal 16 so long as sleep mask 16 is generally closely fitting to the area surrounding the eyes. Seal 16 is preferably made from a soft, conforming, hypoallergenic material. The cross-section of seal 16 is preferably rounded as depicted in FIG. 2 so as to provide a comfortable junction between seal 16 and the skin of the user. Seal 16 may be made from such materials as closed or open cell foam, silicon or moisture impermeable fabric.

Retaining member 18 preferably comprises an elastic strap as depicted in FIGS. 1 and 2. Retaining member 18 may however, be constructed of elastic straps, Velcro, temples as used on eyeglasses or any other structure that would appropriately retain sleep mask 12 in a comfortable position in apposition to the face of the user.

Moisture reservoir 14 is preferably made from an absorbent material, which readily allows for evaporation of water or other evaporative liquids. A sublimating solid may be employed as well. Moisture reservoir 14 may include two layers, an inner layer 24 and a moisture layer 26. Inner layer 24 is preferably a lint free material with antibacterial, antifungal and wicking properties. Moisture layer 26 is preferably made up of an absorbent material. The absorbent material may include super absorbent particles or a jellified water product. Moisture reservoir 14 is preferably removably attachable to sleep mask 12. Attachment between moisture reservoir 14 and sleep mask 12 may be achieved by pressure sensitive adhesive backing, Velcro or any other attachment mechanism known to the removable attachment arts.

Moisture reservoir 14 may be provided in the dry state and moistened at the time of desired use. Moisture reservoir 14 may also be provided pre-moistened in a sealed container. Moisture reservoir 14 may be moistened with, for example, purified water, Ringer's solution, or a buffered purified formulation of an appropriate ionic and electrolytic composition to mimic human tears.

Figure 3:
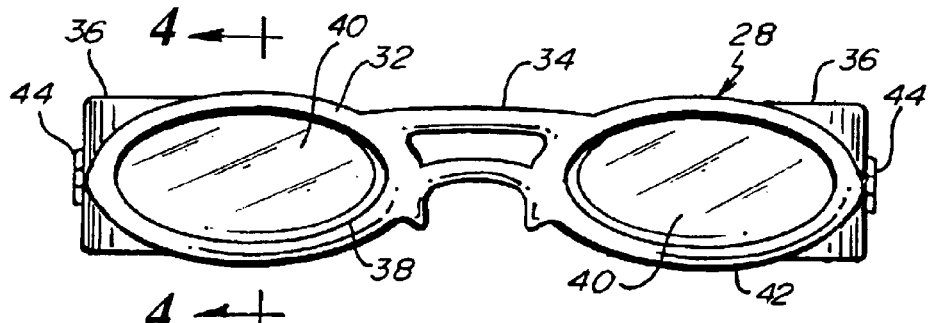
FIG. 3 is a rear plan view of a second embodiment of the pre-corneal humidity chamber.
Figure 4:
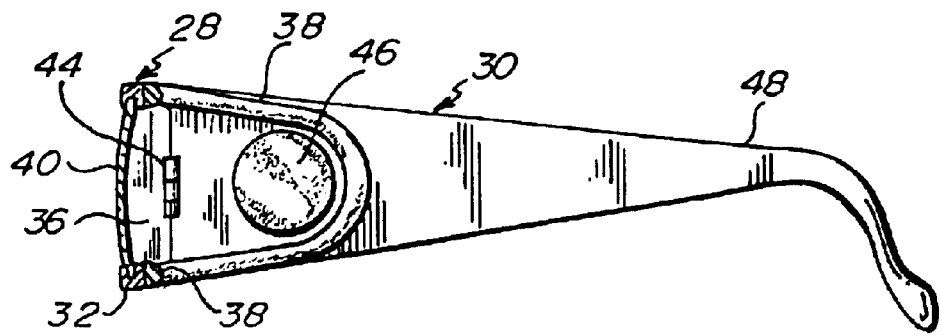
FIG. 4 is an elevational and sectional view of the pre-corneal humidity chamber of FIG. 3.

Referring to FIGS. 3 and 4, another embodiment of the invention is depicted. This embodiment of the pre-corneal humidity chamber 10 generally includes a frame front 28 and temples 30. Frame front 28 and temples 30 may be structured in a fashion generally similar to conventional eyeglasses or in a fashion generally similar to a goggle. This description will be most appropriate for an embodiment of the pre-corneal humidity chamber 10 structured similarly to a conventional pair of eyeglasses, however, this should not be considered limiting. One skilled in the art will readily realize that the general principal can be adapted to any sort of eyewear construction.

Frame front 28 generally includes eye wire 32, bridge 34, end piece 36 and seal 38. Each eye wire 32 encloses and supports lens 40. Lens 40 may be a prescription or nonprescription lens. Lens 40 may also be a colorless transparent lens or a tinted lens. Frame front 28 is constructed to conform generally to the contours of the user's face. Seal 38 preferably runs around the perimeter 42 of frame front 28.

Seal 38 can be constructed of any soft pliable, moisture impermeable material and serves to seal the juncture between frame front 28 and the face of the user. Referring particularly to FIG. 4, temples 30 generally include hinge 44, moisture reservoir 46, earpiece 48, and a portion of seal 38. Seal 38 preferably continues from frame front 28 to enclose moisture reservoir 46 within the same space that the user's eyes are enclosed in. Temples 30 are mirror images of one another and join frame front 28 at hinge 44. Hinge 44 is made of two halves one connected to end piece 36 and one connected to temple 30. Moisture reservoir 46 is similar in structure to moisture reservoir 14 of the previous embodiment. Moisture reservoir 46 conveniently may be attached to temples 30 but may be incorporated into any part of the pre-corneal humidity chamber 10 that allows evaporation in to the enclosure including the eyes.

It will be apparent to one skilled in the art that the embodiment depicted in FIGS. 3 and 4 can readily be modified to treat only one eye as can the embodiment depicted in FIGS. 1 and 2.

Figure 5:
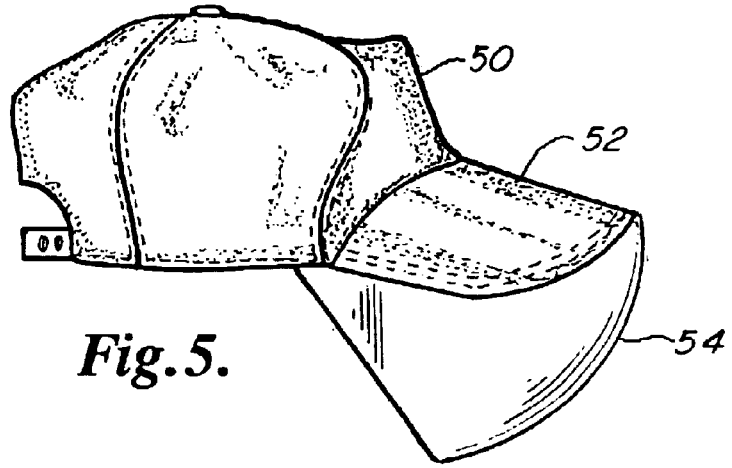
FIG. 5 is an elevational view of a third embodiment of the pre-corneal humidity chamber.
Figure 6:
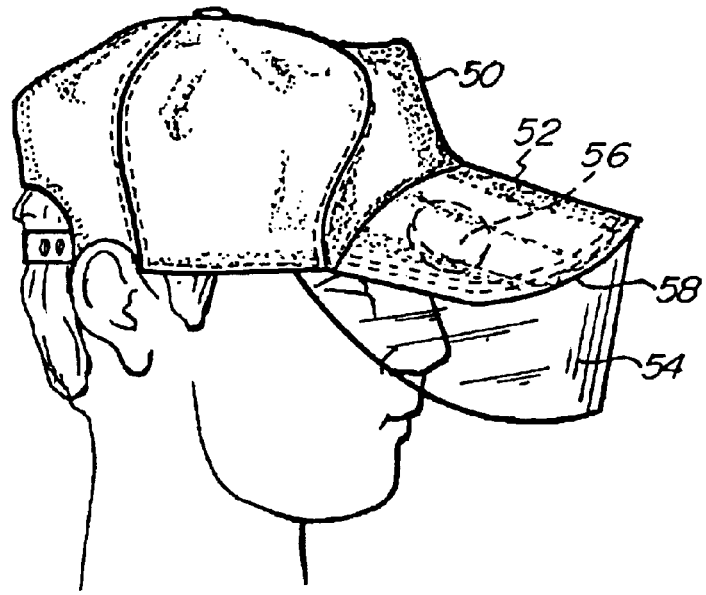
FIG. 6 is a perspective view of the pre-corneal humidity chamber depicted in FIG. 5 with a reservoir shown in phantom.

Referring to FIGS. 5 and 6, another embodiment of pre-corneal humidity chamber 10 is depicted. This embodiment of the invention generally includes hat 50, brim 52, transparent enclosure 54 and moisture reservoir 56.

Hat 50 is preferably a baseball style cap but may include any hat or visor having a brim. Brim 52 may be of any shape or size so long as it protrudes forward of the brow on the front of the hat 50.

Transparent enclosure 54 is preferably an optically clear material. Transparent enclosure 54 extends downward from brim 52 and is configured to fit closely to the face and temples of the user. Transparent enclosure 54 is preferably made from an optically clear transparent material such as polycarbonate or acrylic.

Moisture reservoir 56 is preferably secured to the under side 58 of brim 52. Moisture reservoir 56 may also be incorporated anywhere within transparent enclosure 54. Moisture reservoir 56 may also be secured to transparent enclosure 54. In addition, moisture reservoir 56 may be an integral part of brim 52 or hat 50.

Moisture reservoir 56 may be constructed of a fibrous absorbent polymer, which absorbs water. Moisture reservoir 56 may also be made up of super absorbent particles or a jellified water product as indicated in the embodiments above.

In operation, the pre-corneal humidity chamber 10 is worn by the user so as to enclose the user's eyes. Prior to wearing, the user applies a moisturizing compound such as water, Ringer's solution or an artificial tear solution to moisture reservoir 14, moisture reservoir 46 or moisture reservoir 56. Any of moisture reservoirs 14, 46 or 56 may be supplied in a dry state and moistened at the time of use or may be supplied in a pre-moistened state sealed in a package and applied at the time of desired use.

Referring to FIGS. 1 and 2, sleep mask 12 is applied over the eyes prior to going to sleep. The evaporation of moisture from moisture reservoir 14 provides a high humidity ambient environment around the eyes, thus, reducing evaporation of the watery portion of the tears, thus enhancing the ability of the patient's tears to provide a comfortable environment for the eyes.

In addition, sleep mask 12 may be provided with a moisture reservoir 14 capable of holding a large volume of liquid in order to provide a long-term warm moist soak for the eyes. This approach may be used as an adjunct to the treatment of blepharitis. Referring to FIGS. 3 and 4, this embodiment of the pre-corneal humidity chamber 10 is worn in a fashion similar to eyeglasses or conventional goggles. Prior to wearing, moisture reservoir 46 is replaced if premoistened or moistened. Moisture reservoir 46 then evaporates moisture to provide a high humidity environment for the eyes within the pre-corneal humidity chamber 10. In addition, the pre-corneal humidity chamber 10 of this embodiment provides protection of evaporation caused by air movement. In addition, pre-corneal humidity chamber 10 of this embodiment tends to exclude atmospheric irritants and other air quality irritants that may irritate the eye.

Referring to FIGS. 5 and 6, prior to wearing this embodiment of the pre-corneal humidity chamber 10, moisture reservoir 56 is moistened or inserted if premoistened. This embodiment of the pre-corneal humidity chamber 10 also tends to protect from increased evaporation due to air movement as well as tending to exclude irritants in the ambient air.

In testing an exemplary reservoir was placed in a sealed plastic bag. The humidity within the bag rose to in excess of 90% and remained at that level for over eight hours. This is long enough to provide comfort during a normal sleep cycle. A test subject reported dramatically improved comfort during sleep using an embodiment of the invention.

The present invention may be embodied in other specific forms without departing from the spirit of any of the essential attributes thereof, therefore, the illustrated embodiments should be considered in all respects as illustrative and not restrictive, reference being made to the appended claims rather than to the foregoing description to indicate the scope of the invention.

What is claimed is:

1. A device to improve the comfort and ocular health of a dry eye syndrome subject and to reduce the harmful effect of dry eye syndrome on the eye and adnexa, the device comprising:

an at least partially enclosed chamber adapted to fit closely to an area surrounding the eye of the dry eye syndrome subject, and thereby to create a local atmospheric microenvironment in the vicinity of at least one eye of the dry eye syndrome subject;

the chamber comprising a substantially optically transparent portion supported beneath a substantially opaque brim structure; and a reservoir adapted to contain a material subject to vaporization, the reservoir being adapted to release the material in a vaporized state into the local atmospheric microenvironment so as to expose the eye to the vaporized material to ameliorate the negative effects of the dry eye syndrome.

2. The device as claimed in claim 1, in which the reservoir comprises an absorbent layer.

3. The device as claimed in claim 1, in which the reservoir comprises a first absorbent layer and a second layer having wicking and anti-microorganism properties.

4. The device as claimed in claim 1, in which the reservoir comprises super absorbent particles.

5. The device as claimed in claim 1, in which the reservoir comprises a jellified water product.

6. The device as claimed in claim 1, in which the reservoir is supplied dry and moistened at the time of desired use.

7. The device as claimed in claim 1, in which the reservoir is supplied in a premoistened state in a sealed package.

8. The device as claimed in claim 1, in which the reservoir is moistened with a liquid selected from a group consisting of water, purified water, Ringer's solution and a buffered formulation of an appropriate ionic and electrolytic composition to mimic human tears.

9. The device as claimed in claim 1, in which the enclosed chamber is substantially sealed to the face of the dry eye syndrome subject to contain the microenvironment.

10. The device as claimed in claim 1, in which the enclosed chamber further comprises a conforming seal adapted to substantially seal to the face of the dry eye syndrome patient.

11. The device as claimed in claim 1, in which the reservoir is removably attachable within the enclosed chamber.

12. The device as claimed in claim 1, in which the enclosed chamber further comprises a hat supporting the brim.

13. The device as claimed in claim 1, in which the optically transparent portion comprises a first edge suspended from the brim and enclosing the face, and a second edge closely approximating the face and the reservoir being removably attachable within the enclosure.

14. The device as claimed in claim 1, in which the reservoir is supplied dry along with a premeasured quantity of the material subject to vaporization and the material subject to vaporization is applied to the reservoir at the time of desired use.

15. The device as claimed in claim 1, in which a humidity level achieved within the microenvironment exceeds 90% relative humidity.

16. The device as claimed in claim 1, in which a humidity level achieved within the microenvironment exceeds 90% relative humidity and is maintained for in excess of 6 hours.

17. A method for ameliorating the effects of dry eye syndrome on eyes, the method comprising the steps of:

substantially enclosing the eyes and adnexa in a chamber adapted to fit closely to a face of a dry eye syndrome patient thereby creating a local atmospheric microenvironment in the vicinity surrounding an eye the chamber comprising a substantially optically transparent portion supported beneath a substantially opaque brim structure;

placing within the chamber a reservoir adapted to contain a material subject to vaporization, the reservoir being adapted to release the material in a vaporized state into the local atmospheric microenvironment; and thereby, maintaining within the local atmospheric microenvironment, an atmosphere rich in a vaporized substance that provides beneficial effect to the eyes.

18. The method as claimed in claim 17, further comprising the step of removably attaching the reservoir within the microenvironment.

19. The method as claimed in claim 17, further comprising the step of covering the reservoir with a permeable layer having anti-microorganism properties.

20. The method as claimed in claim 17, further comprising the steps of encapsulating the reservoir in an impermeable package in a premoistened state and opening the impermeable package when it is desired to use the reservoir.

21. The method as claimed in claim 17, further comprising the step of moistening the reservoir with a liquid selected from a group consisting of water, purified water, Ringer's solution and a buffered formulation of an appropriate ionic and electrolytic composition to mimic human tears.

22. The method as claimed in claim 17, further comprising the step of substantially sealing the chamber to the face with a conforming seal.

23. The method as claimed in claim 17, further comprising the step of adapting the chamber to be incorporated into a hat.

24. The method as claimed in claim 17, in which the in which a humidity level achieved within the microenvironment exceeds 90% relative humidity.

25. The method as claimed in claim 17, in which a humidity level achieved within the microenvironment exceeds 90% relative humidity and is maintained for in excess of 6 hours.

26. A device to improve the comfort of a dry eye syndrome patient and to reduce the harmful effect of dry eye syndrome on the eye and adnexa, the device comprising:

optically transparent means for substantially enclosing and fitting closely to an area surrounding the eye of the dry eye syndrome patient thereby creating a local atmospheric microenvironment in the vicinity of at least one eye of the dry eye syndrome patient;

means for shading the eyes from light from above and means for containing a material subject to vaporization, the material containing means being adapted to release the material in a vaporized state into the local atmospheric microenvironment so as to expose the eye and adnexa to the vaporized material to ameliorate the negative effects of the dry eye syndrome.

27. The device as claimed in claim 26, in which the means for containing is removably attachable within the means for enclosing and fitting closely.

28. The device as claimed in claim 26, in which the means for containing comprises an absorbent layer.

29. The device as claimed in claim 26, in which the means for containing comprises a first absorbent layer and a second layer having wicking and anti-microorganism properties.

30. The device as claimed in claim 26, in which the means for containing comprises super absorbent particles.

31. The device as claimed in claim 26, in which the means for containing comprises a jellified water product.

32. The device as claimed in claim 26, in which the means for containing is supplied dry and moistened at the time of desired use.

33. The device as claimed in claim 26, in which the means for containing is supplied in a premoistened state in a sealed package.

34. The device as claimed in claim 26, in which the means for containing is moistened with a liquid selected from a group consisting of water, purified water, Ringer's solution and a buffered formulation of an appropriate ionic and electrolytic composition to mimic human tears.

35. The device as claimed in claim 26, in which the means for enclosing is substantially sealed to the face of the dry eye syndrome patient to contain the microenvironment.

36. The device as claimed in claim 26, in which the means for enclosing further comprises a conforming seal adapted to substantially seal to the face of the dry eye syndrome patient.

37. The device as claimed in claim 26, in which the means for enclosing further comprises a hat.

* * * * *